United States Patent [19]

Tobkes et al.

[11] 4,291,026

[45] Sep. 22, 1981

[54] ANTIBIOTIC BM123ν PAMOATE COMPLEXES

[75] Inventors: Martin Tobkes, Spring Valley; Murray Dann, Pearl River, both of N.Y.; Irving Klothen; Larry D. Spicer, both of Princeton, N.J.; David R. Williams, Stony Point, N.Y.

[73] Assignee: American Cyanamid Company, Stamford, Conn.

[21] Appl. No.: 70,460

[22] Filed: Aug. 28, 1979

[51] Int. Cl.$^3$ .............................................. A61K 31/71
[52] U.S. Cl. .................................. 424/181; 536/17 R
[58] Field of Search ........................... 536/17; 424/181

[56] References Cited

U.S. PATENT DOCUMENTS 4,007,167  2/1977  Martin et al. ..................... 536/17

*Primary Examiner*—Jerome D. Goldberg
*Attorney, Agent, or Firm*—Norton S. Johnson

[57] ABSTRACT

This disclosure describes reversible complexes made from antibiotic trans-BM123ν and water soluble pamoate salts and a process for preparing same. These highly stable complexes are useful as animal feed supplements which significantly enhance the growth rate of animals and poultry.

12 Claims, No Drawings

ANTIBIOTIC BM123ν PAMOATE COMPLEXES

BRIEF SUMMARY OF THE INVENTION

This invention relates to a method of recovering antibiotic trans-BM123ν in a stable form from fermentation whole harvest mashes containing it. More particularly, the process involves adding water soluble pamoate salts generally in the form of ammonium pamoate, alkali metal pamoate or alkaline earth metal pamoate either to the whole harvest mash or to the filtered fermentation liquor, and recovering the so precipitated antiobiotic-pamoate complex (or mixture of complexes) by any convenient means. The invention also relates to the use of the so prepared stable and reversible complexes in animal feed supplement compositions for enhancing the growth rate of animals such as poultry, swine, early weaned pigs, and ruminants such as cattle, sheep and goats.

DETAILED DESCRIPTION OF THE INVENTION

Antibiotic trans-BM123ν is formed by fermentative biosynthesis during the cultivation under controlled conditions of new strains of an undetermined species of Nocardia NRRL 5646, NRRL 11230 and mutants thereof. The preparation and properties of antibiotics trans-BM123$ν_1$, trans-BM123$μ_2$, and trans-BM123ν are set forth in U.S. Pat. No. 4,007,167 which is hereby incorporated by reference. Hereinafter, trans-BM123ν refers to a mixture in any proportions of trans-BM123$ν_1$ and trans-BM123$ν_2$. The problem of recovering the antibiotic economically has been a serious one. In the patent referred to above, the antiobiotics were recovered by ion exchange and carbon column chromatography. Such a process is not excessively expensive when pure antibiotic is required for medical usage. However, when the antibiotic is to be used in animal feed supplement compositions the factor of cost is a very serious matter and there is therefore, a need for an inexpensive process of recovering the antibiotic for this purpose. U.S. applications Ser. Nos. 874,306; 874,307; and 874,308 are directed to processes of such antibiotic removal.

The present invention deals with a process and a product. The process involves the precipitation of the antiobiotic BM123ν from an aqueous solution containing such antibiotic. Particularly, such solutions are whole harvest mashes and filtrates thereof, and the precipitating agent is a water soluble form of pamoic acid of the formula:

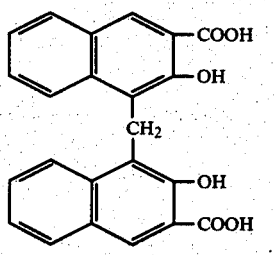

The water soluble forms of pamoic acid, being those with sufficient water solubility to precipitate BM123ν include in addition to the free acid, the ammonium salt, alkali metal salts, alkaline earth metal salts as well as amines, including for example, those of the mono-, di-, or tri-lower alkyl, and aryl amines. It should be understood that the term "alkali metals" means those elements from the first group of the periodic table of the elements. Similarly, the term "alkaline earth metals" is meant to include those of the second group of the periodic table of the elements.

The process of this invention begins with the dissolution of a water soluble pamoate salt. This is followed by the complexing of the disassociated pamoic ion and the BM123ν molecule. Therefore, the specific pamoic acid or salt selected would best be chosen on the bases of solubility, cost, and toxicity and does not alter the basic inventive concept. For simplification of terminology the entire group of water soluble pamoic acid salts (as well as pamoic acid) described above will be referred to as water soluble pamoate salt(s), which is to include mixed such pamoate salts.

From the above considerations it will be clear to those skilled in the art that ammonium pamoate and sodium pamoate to include both mono- and di- forms are the more preferred water soluble pamoate salts.

The novel process of the present invention provides almost complete removal of the antibiotic activity from the fermentation mash or broth. Furthermore, the antiobiotic-pamoate complex so obtained can be used without separation of the constituents in animal feed supplement compositions, which is an important economic advantage. Therefore, in one of the aspects of the present invention the complex of antibiotic trans-BM123ν and a pamoate moiety is included as a product.

A particularly surprising result of this process is the extreme stability of this complex over other BM123ν complexes. In accelerated storage life tests the BM123ν-pamoate complex [isolated as in Example 1] retained 70% activity at 70° C. for 8 hours time. Under similar conditions a BM123ν lauryl sulfate complex preparation retained 18% activity.

The product of the antibiotic and water soluble pamoate salts has been referred to as a reversible antibiotic-pamoate complex. Its exact chemical nature has not been determined, but covalent bonding is not involved and the product is not a physical mixture. This complex, derived from the interaction of the antibiotic and water soluble pamoate salts is not necessarily combined in any limiting stoichiometry. Some tests on the pure complex have indicated a stoichiometry of 1.5 moles of pamoic acid/mole BM123ν. The chemical bonds are reversible since the antibiotic trans-BM123ν may be recovered from the complex by various means such as leaching with mineral acid. While it is not intended to limit the present invention to theories of chemical constitution and the like, it seems probable that the complex of the present invention is sufficiently reversible so that under conditions of use in animal feed supplement compositions the antibiotic is set free upon ingestion.

As starting material for the novel process of the present invention there may be employed the whole harvest mesh obtained after completion of a fermentation with Nocardia sp. NRRL 5646, NRRL 8050, NRRL 11230 or mutants thereof. Preferably, there is employed the fermentation liquor or broth which has been clarified by removing the mycelia and other insolubles by filtration. Diatomaceous earth or any other conventional filtration aid may be used to assist in the filtration. Ion exchange resin clarification as in Examples 2 and 3 is also helpful. In general, the pH of the whole mash or of the filtered broth at ambient temperature is first adjusted to between about 4 and 8, by the addition of dilute acid or base. Suitable acids for this purpose may be, for example, hydrochloric acid, sulfuric acid, trifluoroacetic acid, and the like, although even glacial acetic acid may be used. Suitable bases include ammonium hydroxide and the alkali and alkaline earth hydroxides, carbonates and bicarbonates. Then, an aqueous solution of the water soluble pamoate salt or salts is added slowly, with stirring, at ambient temperatures. The entire process of the present invention is preferably carried out at from about 5° C. to about 30° C., conveniently at room temperature. The antibiotic and pamoate salt form a complex which is water insoluble and thus precipitates. The precipitated complex or, in the case of the whole mash, the precipitated complex together with the fermentation mash solids, is then dried or removed by filtration or centrifugation and dried. The products so obtained may be dried by (1) slurrying the wet solids in polar, water miscible non-solvents such as acetone followed by filtration, rinsing and air-drying; or by (2) reslurrying the wet solids in water and freeze drying or spray drying.

When the products of the present invention are thus carefully dried under temperature conditions which do not degrade antibiotic trans-BM123$\nu$, they are usually gray to tan to brown solids in the case of the pamoate complex. In the dry form, these products are extremely stable, keeping without significant loss of antibiotic activity for considerable periods of time especially as compared to other BM123$\nu$ salts. This long storage life is, of course, an important practical advantage over the prior art.

It is an advantage of the process of the present invention that the amount of water soluble pamoate salts added to precipitate the complex with the antibiotic is not critical. The trans-BM123$\nu$ content of the whole mash may be readily determined by microbiological assay as set forth in U.S. Pat. No. 4,007,167. The preferred method is an adaptation of the *Staphylococcus aureus* tubidimetric assay for tetracycline that is described in "Assay Methods of Antibiotics, a Laboratory Manual" by Grove & Randall, Medical Encyclopedia, Inc. (1955) pages 48–52, substituting Klebsiella pneumoniae as the test organism. The required amount of water soluble pamoate salts is then preferably dissolved or suspended in a convenient quantity of water and the aqueous solution or suspension is added to the whole mash as described above. Excess water soluble pamoate salts present will merely remain in solution upon filtration.

In general, the amount of water soluble pamoate salts required to precipitate antibiotic trans-BM123$\nu$ from a clarified liquor is about 0.75–2.0 gram per gram of trans-BM123$\nu$ activity is the clarified liquor. A higher level of water soluble pamoate salts required to precipitate trans-BM123$\nu$ from whole mash than from clarified liquor is due to coprecipitation of other basic material present in the whole mash. Conveniently, the minimum amount of water soluble pamoate salts required to form the complex with the antibiotic in the clarified liquor from any particular fermentation batch may be readily determined as follows. A sample (conveniently 50–100 ml.) of the fermentation whole harvest mash is taken and clarified by removing the mycelia and other insolubles by filtration, preferably with a filter aid. The filtrate is then adjusted to a pH of 4.0 to 8.0 with dilute aqueous mineral acid or base, and then titrated with the particular water solution of pamoate which is to be used, until no further precipitate or turbidity forms. The amount of pamoate solution for the fermentation batch is then calculated from the titer of the sample taken, providing also for a slight excess.

This invention also relates to animal feed supplement compositions effective in accelerating the growth rate of animals and poultry. In recent years the use of antibiotics in animal feeds for improving growth characteristics and efficiency of feed utilization has become of considerable economic importance. In accordance with the present invention, the dried pamoate complex or the dried harvest mash solids containing the pamoate complex, either alone or in combination with suitable carriers, when added to an animal feed, aid in increasing the growth rate. In addition, feed efficiency is improved. The present invention has the advantage that the growth rate of non-ruminants such as poultry and swine and especially weanling pigs is significantly increased, and that feed conversion rates are noticeably enhanced.

While it is known that BM123$\nu$ and certain pharmaceutically acceptable salts and complexes of said antibiotic are effective for enhancing the growth rate of animals and improving efficiency of feed utilization thereby, previously known BM123$\nu$ salts and complexes have not been entirely satisfactory for the above-mentioned utilities, since said known antibiotic salts and complexes show some instability (i.e., loss of efficacy) when stored alone or in the presence of harvest mash solids and/or when prepared as animal feed supplements of finished feeds and stored for extended periods of time.

In contrast, BM123$\nu$ pamoate complexes exhibit excellent stability in harvest mash solids and when admixed with the carriers and diluents normally utilized in the preparation of animal feed supplements, premixes, and finished feeds.

The feed supplement compositions of the present invention are administered in an amount sufficient to furnish approximately the following dosage levels in mg./head/day:

Large ruminants: 350
Small ruminants: 200
Non-ruminants: 100
Poultry: 2

The milligrams per pound of antibiotic trans-BM123$\nu$ present in any particular supplement or premix composition of the present invention may be readily determined by bioassay as set forth in U.S. Pat. No. 4,007,167. From the potency data thus obtained, the pounds of feed supplement composition to be used per ton of feed may be readily calculated. A wide variety of carriers may be used in the preparation of the feed supplement compositions of this invention containing the dried pamoate complex or the dried harvest mash solids containing the pamoate complex. Carriers suitable for use to make up the feed premix compositions include the following: soybean meal, alfalfa meal, cotton seed oil meal, linseed oil meal, cornmeal, corncob meal, and the like. The carrier promotes a uniform distribution of the complex in the finished feed into which the supplement is blended. It thus performs an important function by ensuring proper distribution of the complex throughout the feed.

For a clearer understanding of the invention, specific examples of it are set forth below. These examples are merely illustrative, and are not to be understood as limiting the scope and underlying principles of the invention in any way.

EXAMPLE 1

Precipitation of Antibiotic BM123ν Pamoate From Whole Harvest Mash

To 100 ml. of stirred fermentation mash containing BM123ν there is added 15 ml. of a 10% w/v solution of sodium pamoate while maintaining the pH at 4.7 by the simultaneous addition of 50% sulfuric acid. After stirring 5 minutes, the suspension is centrifuged and after removing the supernatant the residue is dried in vacuo at 40° C. to give 5.59 g. of a solid which bioassays 3.21 mcg./mg. as BM123ν in an auto turbidimetric method against *Klebsiella pneumoniae.*

EXAMPLE 2

Preparation of Antibiotic BM123ν Pamoate Complex From Harvest Mash Filtrate

To a 320 liter portion of fermentation mash containing BM123ν at pH 5.2, is added 640 g. (0.2%) of sodium fluoride. The pH is adjusted to 6.0-6.25 with sodium hydroxide and the mixture is stirred for one hour. A 16 kg. portion of filter aid (Hydro-Supercel, Johns-Manville) is added and the mixture is filtered. The filtrate is adjusted to pH 4.7-4.8 with hydrochloric acid and 6400 ml. of Amberlite IRC-72 (Na+) resin (Rohm & Haas, Inc.) is gradually added. The pH is adjusted to 4.7-4.9 with hydrochloric acid, the mixture is stirred for 2 hours and allowed to stand overnight. The supernatant is syphoned off and discarded. The resin is transferred to a 10.16 cm.×121.92 cm. glass column having a bed volume of about 4.8 liters. The bed is washed with two bed volumes of pH 4.5 sodium acetate-acetic acid buffer solution (8 g. of sodium acetate per liter of water adjusted to pH 4.5 with glacial acetic acid). Then the resin is washed with two additional bed volumes of the same buffer and this wash is collected separately, adjusted to pH 4.0 with glacial acetic acid and put through the resin bed again. The resin is then washed with 20 liters of water. The antibiotic activity is eluted from the column with 0.02-0.025 N hydrochloric acid, collecting one liter fractions and monitoring the fractions by ultraviolet absorption at 286 nm for antibiotic activity. A total of 97 liters of active eluate are pooled. Thirty-two liters of this clarified eluate are adjusted from pH 2.1 to pH 4.7-4.8 with sodium hydroxide and 480 g. of perlite filter aid are added. A solution of 50 g. of pamoic acid disodium salt in 625 ml. of water is prepared and a total of 555 ml. is added in approximately 50 ml. increments, adjusting the pH to 4.7-4.8 with 10 N sulfuric acid after each addition. A 480 g. portion of perlite is added and the mixture is filtered on a filter press. The damp cake is dried in a vacuum oven at 38°-40° C. and then ground in a comminuting machine giving 997 g. of product which bioassayed 3.5% as BM123ν in an auto turbidimetric method against *Klebsiella pneumoniae.*

EXAMPLE 3

Preparation of Antiobiotic BM123 Pamoate Complex From Harvest Mash Filtrate

To a 3000 liter portion of fermentation mash containing BM123ν is added 6 kg. of sodium fluoride. The mixture, at pH 5.5-6.5, is stirred for about ½ hour and 150 kg. of filter aid (Hydro-Supercel) is added. The mixture is filtered through a plate-frame filter press. The first 700 liters of clarified filtrate are collected and adjusted to pH 4.5-4.8 with hydrochloric acid. The antibiotic activity is absorbed batchwise with Amberlite IRC-72 (Na+) (Rohm & Haas, Inc.) resin used at a rate of 30 ml. of resin/liter of filtrate. The resin is added gradually to the filtrate with constant stirring and the pH of the mixture is maintained at 4.5-4.8 with hydrochloric acid. After addition is complete, the mixture is stirred for about 3 hours and the resin is allowed to settle overnight. The supernatent is syphoned off and the 17.9 liters of resin are transferred to a 15.24 cm.×152.4 cm. glass column. The resin is washed with two bed volumes of sodium acetate-acetic acid buffer (8 g. of sodium acetate per liter of water, adjusted to pH 4.0 with glacial acetic acid). This wash is repeated with a fresh two bed volume of the buffer. This second wash is collected, adjusted to pH 4.0 with glacial acetic acid, and again passed through the resin. The resin is washed with four bed volumes of water and then eluted with 0.03-0.05 N hydrochloric acid monitoring for activity by ultraviolet absorption of 286 nm. The active fractions are pooled, adjusted to pH 5.0-5.3 by addition of Amberlite IRA-45 resin (Rohm & Haas, Inc.). After standing, the supernatant is syphoned off and concentrated at reduced pressure to a volume of 12 liters. A 2 liter portion of this clarified concentrate is adjusted to pH 4.7-4.8 with 10 N sulfuric acid. To this is added, in increments, a solution of 125 g. of pamoic acid disodium salt in 1562.5 ml. of water, with constant stirring, maintaining the pH at 4.7-4.8 with 10 N sulfuric acid. The precipitate is collected by centrifugation, suspended in water and freeze-dried, giving 215.5 g. of dried product which bioassays 27% as BM123ν in an auto turbidmetric method against *Klebsiella pneumoniae.*

EXAMPLE 4

BM123ν Pamoate Complex Recovery at Higher pH

The precipitation of BM123ν pamoate complex is investigated at pH 5, 6, 7, and 8. To 100 ml. aliquots of mash filtrate clarified as in Example 3 is added 2.0 ml of a 10% aqueous solution of disodium pamoate with stirring.

(a) in one aliquot the pH is adjusted to 5.0 with 0.1 normal hydrochloric acid and after 20 minutes stirring the mixture is centrifuged. Upon removal of the supernatant the residue is dried in vacuo at 30° C. to offer about a 21% yield of available BM123ν which complex by turbidimetric assay is 24 micrograms/mg as to BM123ν hydrochloride equivalent.

(b) in one aliquot the adjustment is to pH 6.0 with 0.1 normal sodium hydroxide. The yield is about 94% of available BM123ν which complex by turbidimetric assay is 364 micrograms/mg as to BM123ν hydrochloride equivalent.

(c) in one aliquot the adjustment is to pH 7.0 with 0.1 normal sodium hydroxide. The yield is about 85% available BM123 which complex by turbidimetric assay is 320 micrograms/mg as to BM123ν hydrochloride equivalent.

(d) in one aliquot the adjustment is to pH 8.0 with 0.1 normal sodium hydroxide. The yield is about 63% of available BM123ν which complex by turbidimetric assay is 145 micrograms/mg as to BM123 hydrochloride.

EXAMPLE 5

Preparation of Antibiotic BM123ν Sodium Pamoate Complex

A 7.00 g. portion of antibiotic BM123ν is dissolved in 200 ml. of water. A total of 70 ml. of 7.5% w/v sodium pamoate solution at pH 10.2 is added, the pH is adjusted to 4.75 with 10 N sulfuric acid and the mixture is centrifuged. The precipitate is dried in vacuo at room temperature and assayed turbidimetrically at 512 mcg./mg. antibiotic BM123ν.

EXAMPLE 6

Precipitation of Antibiotic BM123ν Pamoate From Harvest Mash Filtrate

To 600 ml. of stirred fermentation mash containing BM123ν there is added diatomaceous earth and the mixture is filtered. To 100 ml. of this clarified filtrate there is added with stirring, 15 ml. of a 10% w/v solution of sodium pamoate while simultaneously maintaining the pH of the mixture at 4.7 by the addition of 50% sulfuric acid. The resultant precipitate is centrifuged off and dried in vacuo at 40° C. to give 4.75 g of product which bioassays 3.07 mcg./mg. as BM123 in an auto turbidimetric method against *Klebsiella pneumoniae*.

EXAMPLE 7

Growth Promoting Effect of Antibiotic BM123ν Pamoate Complex on Poultry

One day old Hubbard x Ross crossbred chicks are used. These chicks are randomly allotted to pens of ten chicks (5 male and 5 female) each. In each experiment three pens of chicks are used for unmedicated controls and for each level of drug, and pens of chicks used at 120 ppm BM123 pamoate complex. The duration of each experiment is 14 days.

The controls are offered an unmedicated diet of broiler ration (composition follows) and water ad libitum. The medicated chicks are offered the same diet containing antibiotic BM123ν pamoate complex at a level of 20 parts per million and water ad libitum. The weight of the chicks is determined at the beginning and on completion of the experiments. Weight gain and the amount of feed consumed are also determined. The data are averaged and summarized in Table I below, together with the percent improvement in weight gains and feed/gain ratios.

Broiler Ration Formula:

| Component | Percent by weight |
|---|---|
| Ground yellow corn | 53.45 |
| Soybean oil meal (49%) | 28.00 |
| Menhaden fish meal (60%) | 5.00 |
| Corn Gluten meal (60%) | 5.00 |
| Dehydrated alfalfa meal (17%) | 2.00 |
| Stabilized fat | 4.00 |
| Dicalcium phosphate | 1.20 |
| Ground limestone | 0.50 |
| Sodium chloride | 0.30 |
| Trace minerals mixture* | 0.05 |
| Vitamin premix** | 0.50 |

*Trace Mineral Mixture

| Component | | One lb/ton Furnishes |
|---|---|---|
| Manganese | 12.50% | 62.5 ppm. |
| Iron | 6.00% | 30.0 ppm. |
| Lime | 5.00% | 25.0 ppm. |
| Copper | 0.65% | 3.25 ppm. |
| Iodine | 0.35% | 1.75 ppm. |
| Cobalt | 0.25% | 1.25 ppm. |
| Calcium (min. 15.30%, max. 18.35%) | | |

**Vitamin Premix for One Ton

| Component | Weight In gm. |
|---|---|
| Dl methionine | 453.6 |
| Butylated hydroxy toluene | 113.6 |
| Vitamin A (30,000 mcg./g.) | 100.0 |
| Vitamin D$_3$ (200,000 mcg./g.) | 5.0 |
| Vitamin E (20,000 mcg./lb.) | 45.4 |
| Riboflavin | 4.0 |
| Niacinamide | 25.0 |
| Calcium pantothenate | 8.0 |
| Vitamin K (menadione) | 1.0 |
| Folic acid (10%) | 13.0 |
| Choline chloride (50%) | 908.0 |
| Vitamin B$_{12}$ (20 mg./lb.) | 227.0 |
| Corn oil | 50.0 |
| Fine ground corn | 2582.4 |

TABLE I

| Treatment | Drug Level in Feed ppm. | Average Weight Per Chick in Grams | | Average Weight Gain Per Chick in Grams | Feed Consumed Per Chick in Grams (Average) | Feed/Gain Ratio | % Improvement Over Control in | |
|---|---|---|---|---|---|---|---|---|
| | | Start | End | | | | Weight Gain | Feed/Gain Ratio |
| Control | 0 | 36.3 | 238.7 | 202.5 | 321.2 | 1.586 | — | — |
| Antibiotic BM123γ pamoate complex | 20 | 36.2 | 260.6 | 224.4 | 340.0 | 1.533 | 10.8 | 3.3 |
| Antibiotic BM123γ pamoate complex | 20 | 36.2 | 257.7 | 221.5 | 338.0 | 1.526 | 9.4 | 3.8 |
| Control | 0 | 39.7 | 249.7 | 210.0 | 338.1 | 1.610 | — | — |
| Antibiotic BM123γ pamoate complex | 20 | 39.7 | 267.7 | 228.0 | 352.9 | 1.548 | 8.6 | 3.9 |
| Antibiotic BM123γ pamoate complex | 20 | 36.3 | 251.9 | 215.5 | 331.7 | 1.539 | 6.4 | 3.0 |

EXAMPLE 8

BM123ν Pamoate Complex Stability

A BM123ν pamoate complex, isolated by a procedure similar to that described in Example 1, is "stress-tested" by heating for 8 hours at 70° C. Bioassays show that 70% of the active material remains after stressing. In contrast, when BM123ν is isolated by the addition of sodium lauryl sulfate solution and the resulting BM123ν lauryl sulfate complex "stress-tested" in exactly the same manner, only 18% of the active material can be found by bioassay.

EXAMPLE 9

BM123ν Pamoate Complex Stability

A filtrate containing BM123ν, isolated as described in Example 6, is treated as follows: One portion is spray-dried. A second portion is treated with sodium pamoate solution and the precipitate is isolated by filtration and dried. A third portion is treated with sodium lauryl sulfate solution and the precipitate is filtered and dried. Each of these three products is mixed with animal feed and the mixtures are formed into pellets. The stability of these pellets is summarized below, with the recovery of active BM123ν being expressed as percent recovery of the amount of active ingredient added to the animal feed product.

| Treatment | % Recovery at 37 C. | |
|---|---|---|
| | Two Weeks | Four Weeks |
| Spray-dried | 31 | 17 |
| Sodium lauryl sulfate | 52 | 40 |
| Sodium pamoate | 78 | 51 |

We claim:

1. A process of recovering an antibiotic trans-BM123ν pamoate complex from a fermentation whole harvest mash containing the antibiotic trans-BM123ν which comprises the steps of:
   (a) producing a fermentation liquor by clarifying the whole harvest mash; and
   (b) adding a water soluble pamoate salt selected from the group consisting of ammonium pamoate, alkali metal pamoate, alkaline earth metal pamoate and combinations thereof while maintaining the liquor at a pH of from 4.0 to 8.0 by addition of a pharmacologically acceptable acid, or base, and
   (c) removing the precipitated antibiotic trans-BM123ν pamoate complex; and
   (d) drying the antibiotic trans-BM123ν pamoate complex.

2. The process of claim 1 wherein the water soluble pamoate salt of step (b) is ammonium pamoate.

3. The process of claim 1 wherein the water soluble pamoate salt of step (b) is sodium pamoate.

4. The process of claim 1 wherein the water soluble pamoate salt of step (b) is magnesium pamoate.

5. The process of claim 1 wherein the water soluble pamoate salt of step (b) is calcium pamoate.

6. The dry complex of BM123ν and pamoate prepared as defined in the process of claim 1.

7. A process for the production of a dried fermentation harvest mash solids animal feed supplement containing an antibiotic trans-BM123ν pamoate complex which comprises the steps of:
   (a) adding a water soluble pamoate salt selected from the group consisting of ammonium pamoate, alkali metal pamoate, alkaline earth metal pamoate and combinations thereof to a fermentation whole harvest mash containing antibiotic trans-BM123ν while simultaneously maintaining the pH from 4.0 to 8.0 by adding a pharmacologically acceptable acid, or base; and
   (b) removing the harvest mash solids together with the precipitated antibiotic trans-BM123ν pamoate complex; and
   (c) drying the mixture of mash solids and antibiotic trans-BM123ν pamoate complex.

8. The process of claim 7 wherein the water soluble pamoate salt of step (a) is sodium pamoate.

9. The process of claim 7 wherein the water soluble pamoate salt of step (a) is ammonium pamoate.

10. The process of claim 7 wherein the water soluble pamoate salt of step (a) is pamoic acid.

11. An animal feed composition for improving feed efficiency and enhancing the growth rate of animals and poultry comprising a nutritionally balanced animal feed containing from about 0.0001% to about 1.0% by weight of the feed of an antibiotic trans-BM123ν-pamoate complex prepared in accordance with the process of claim 1.

12. An animal feed premix for improving feed efficiency and enhancing the growth rate of animals and poultry comprising from about 50% to about 99% by weight of an edible carrier and from about 1% to about 50% by weight of an antibiotic ingredient selected from the group consisting of a dry complex prepared in accordance with the process of claim 1 an animal feed supplement as defined in claim 7 and mixtures thereof in any proportion.

* * * * *

UNITED STATES PATENT OFFICE
CERTIFICATE OF CORRECTION

Patent No. 4,291,026     Dated September 22, 1981

Inventor(s) MARTIN TOBKES, MURRAY DANN, IRVING KLOTHEN, LARRY DEAN SPICER, DAVID R. WILLIAMS It is certified that error appears in the above-identified patent and that said Letters Patent are hereby corrected as shown below:

In Col. 1, lines 13, 27, 34, 47; Col. 2, lines 25-26, 56; Col. 5, line 58, replace the word "antiobiotic" with the word -- antibiotic -- .

In Col. 1, line 28, replace "$\mu_2$" with -- $\gamma_2$ -- .

In Col. 3, line 11, replace the word "conventiently" with the word -- conveniently -- .

In Col. 6, line 8, replace the word "supernatent" with the word -- supernatant -- .

Signed and Sealed this

Seventh Day of January 1986

[SEAL]

Attest:

DONALD J. QUIGG

Attesting Officer     Commissioner of Patents and Trademarks